(12) United States Patent
Maitro-Vogel et al.

(10) Patent No.: US 8,987,183 B2
(45) Date of Patent: *Mar. 24, 2015

(54) USE OF OPTIONALLY OXIDIZED THIOETHERS OF POLYALKYLENE OXIDES IN WASHING AND CLEANING COMPOSITIONS

(75) Inventors: Sophie Maitro-Vogel, Mannheim (DE); Jürgen Tropsch, Römerberg (DE); Wolfgang Spiegler, Worms (DE); Roman Benedikt Raether, Speyer (DE)

(73) Assignee: BASF SE, Ludwigshafen (DE)

( * ) Notice: Subject to any disclaimer, the term of this patent is extended or adjusted under 35 U.S.C. 154(b) by 25 days.

This patent is subject to a terminal disclaimer.

(21) Appl. No.: 13/350,046

(22) Filed: Jan. 13, 2012

(65) Prior Publication Data

US 2012/0184478 A1 Jul. 19, 2012

Related U.S. Application Data

(60) Provisional application No. 61/432,232, filed on Jan. 13, 2011.

(51) Int. Cl.

| C11D 17/00 | (2006.01) |
|---|---|
| C11D 1/755 | (2006.01) |
| C11D 1/00 | (2006.01) |
| C07C 317/18 | (2006.01) |
| C07C 323/12 | (2006.01) |

(52) U.S. Cl.
CPC ............... C11D 1/755 (2013.01); C11D 1/002 (2013.01); C07C 317/18 (2013.01); C07C 323/12 (2013.01)
USPC ............ 510/218; 510/424; 510/426; 510/492

(58) Field of Classification Search
None
See application file for complete search history.

(56) References Cited

U.S. PATENT DOCUMENTS

| 3,234,258 A | 2/1966 | Morris |
|---|---|---|
| 3,288,858 A | 11/1966 | Lyness et al. |
| 3,627,845 A | 12/1971 | Hickner et al. |
| 3,887,806 A | 6/1975 | Rodak et al. |
| 4,604,224 A | 8/1986 | Cheng |
| 4,663,082 A * | 5/1987 | Bobsein et al. ............... 510/413 |
| 5,075,041 A | 12/1991 | Lutz |
| 5,227,446 A | 7/1993 | Denzinger et al. |
| 5,266,237 A | 11/1993 | Freeman et al. |
| 5,360,569 A | 11/1994 | Madison et al. |
| 5,399,286 A | 3/1995 | Funhoff et al. |
| 5,506,332 A | 4/1996 | Funhoff et al. |
| 5,593,953 A | 1/1997 | Malchow, Jr. |
| 5,747,635 A | 5/1998 | Kroner et al. |
| 5,756,456 A | 5/1998 | Ho et al. |

FOREIGN PATENT DOCUMENTS

| CA | 2053900 A1 | 10/1990 |
|---|---|---|
| CA | 2038332 A1 | 9/1991 |
| CA | 2065947 A1 | 10/1992 |
| DE | 4106355 A1 | 9/1992 |
| DE | 4313909 A1 | 11/1994 |
| DE | 4415623 A1 | 11/1995 |
| EP | 001004 A1 | 3/1979 |
| EP | 396 303 A2 | 11/1990 |
| EP | 451 508 A1 | 10/1991 |
| EP | 453 003 A2 | 10/1991 |
| EP | 454126 A1 | 10/1991 |
| EP | 511037 A1 | 10/1992 |
| EP | 581452 A1 | 2/1994 |
| EP | 656914 A1 | 6/1995 |
| EP | 0877002 A2 | 11/1998 |
| GB | 643456 A | 9/1950 |
| JP | 58/217598 A | 12/1983 |
| WO | WO-90/13533 A1 | 11/1990 |
| WO | WO-93/02387 A1 | 2/1993 |
| WO | WO-94/01486 A1 | 1/1994 |
| WO | WO-94/21777 A1 | 9/1994 |
| WO | WO-95/07331 A1 | 3/1995 |

OTHER PUBLICATIONS

International Search Report for PCT/EP2012/050422.
U.S. Appl. No. 13/350,169, filed Jan. 13, 2012.

* cited by examiner

*Primary Examiner* — Necholus Ogden, Jr.
(74) *Attorney, Agent, or Firm* — Drinker Biddle & Reath LLP

(57) ABSTRACT

The present invention relates to the use of (oxidized) thioethers of polyalkylene oxides in washing and cleaning compositions, especially in dishwashing compositions, and to washing and cleaning compositions, especially dishwashing compositions, which comprise (oxidized) thioethers of alcohol alkoxylates. These (oxidized) thioethers are especially suitable as surfactants with rinse aid function (rinse aid surfactants). "Oxidized" relates to the sulfur atom in the thioether, which may be present in oxidized form as sulfoxide (SO) or sulfonyl ($SO_2$). The invention also relates to particular oxidized thioethers of polyalkylene oxides.

22 Claims, No Drawings

USE OF OPTIONALLY OXIDIZED THIOETHERS OF POLYALKYLENE OXIDES IN WASHING AND CLEANING COMPOSITIONS

CROSS-REFERENCE TO RELATED APPLICATIONS

This application claims benefit (under 35 USC 119(e)) of U.S. Provisional Application 61/432,232, filed Jan. 13, 2011, which is incorporated by reference.

BACKGROUND OF THE INVENTION

The present invention relates to the use of (oxidized) thioethers of polyalkylene oxides in washing and cleaning compositions, especially in dishwashing compositions, and to washing and cleaning compositions, especially dishwashing compositions, which comprise (oxidized) thioethers of alcohol alkoxylates. These (oxidized) thioethers are especially suitable as surfactants with rinse aid function (rinse aid surfactants). "Oxidized" relates to the sulfur atom in the thioether, which may be present in oxidized form as sulfoxide (SO) or sulfonyl ($SO_2$). The invention also relates to particular oxidized thioethers of polyalkylene oxides.

Surfactants are substances which can lower interfacial tension. Typically, surfactants possess a characteristic structure and have at least one hydrophilic and at least one hydrophobic functional group. When the two parts of the molecule are in equilibrium with respect to one another, the substance will accumulate and become aligned at an interface, i.e. hydrophilic groups point, for example, into an aqueous phase and the hydrophobic groups in the direction of other solid, liquid or gaseous phases. A further special feature of surfactants is the formation of higher aggregates, known as micelles. In these, the surfactant molecules become ordered in such a way that the polar groups, for example, form a spherical surface. This has the effect that substances such as soil particles are solubilized in an aqueous solution with formation of micelles. Surfactants are therefore suitable especially for cleaning surfaces and as an additive in washing compositions.

Surfactants which have a hydrophobic block and a hydrophilic block are widespread. However, their tendency to form foam makes them unsuitable or suitable only to a limited degree for many applications. For applications in which strong foam formation is unwanted, therefore, nonionic surfactants which have a second hydrophobic block have been developed, which limits the foam volume.

The second hydrophobic block can derive, for example, from a fatty alcohol. However, the use of dishwashing compositions which comprise such a surfactant, especially of dishwashing compositions for machine dishwashers, frequently leads to residues remaining on the dishware cleaned therewith (deposit formation; called "spotting" in the case of formation of spot deposits or "filming" in the case of film-like deposits).

The second hydrophobic block can alternatively derive from a fatty acid. In the case of dishwashing compositions which comprise such surfactants, the problem of deposit formation is no longer as great; however, these surfactants are hydrolysis-sensitive due to the ester group, which greatly restricts the usability thereof in alkaline formulations and at relatively high temperatures, especially in prolonged washing operations.

Thioethers of polyalkylene oxides are known, for example from U.S. Pat. No. 5,593,953, where the use thereof as lubricant additives is described, or from WO 93/02387, where they are used in photographic high-contrast elements for prevention of pepper fog. Use as a washing or cleaning composition is not mentioned.

A SUMMARY OF THE INVENTION

It was an object of the present invention to provide compounds which do not have the disadvantages of the prior art surfactants. More particularly, the compounds should have no strong tendency, if any, to foam formation; they should leave behind a lower level of residues, especially filming residues, on the dishware washed therewith, and they should at least be less hydrolysis-labile, if at all, than the surfactants based on fatty acid esters.

The object is achieved by the use of compounds of the formula I

$$R-S(O)_x-[-CH_2CH_2-O-]_n-CH_2CH_2-S(O)_y-R' \quad (I)$$

in which
R and R' are each independently $C_6$-$C_{18}$-alkyl;
n is from 11 to 150; and
x and y are each independently 0, 1 or 2;
in washing or cleaning compositions, especially in dishwashing compositions.

The invention also relates to washing or cleaning compositions, especially dishwashing compositions, comprising at least one compound of the formula I as defined above.

A DETAILED DESCRIPTION OF THE INVENTION

In the context of the present invention, $C_6$-$C_{18}$-alkyl is a linear or branched alkyl radical having 6 to 18 carbon atoms. Examples thereof are hexyl, heptyl, octyl, 2-ethylhexyl, nonyl, decyl, 2-propylheptyl, undecyl, dodecyl, tridecyl, tetradecyl, pentadecyl, hexadecyl, heptadecyl, octadecyl and positional isomers thereof.

$C_8$-$C_{16}$-Alkyl is a linear or branched alkyl radical having 8 to 16 carbon atoms. Examples thereof are octyl, 2-ethylhexyl, nonyl, decyl, 2-propylheptyl, undecyl, dodecyl, tridecyl, tetradecyl, pentadecyl, hexadecyl and positional isomers thereof.

$C_8$-$C_{18}$-Alkyl is a linear or branched alkyl radical having 8 to 18 carbon atoms. Examples thereof are octyl, 2-ethylhexyl, nonyl, decyl, 2-propylheptyl, undecyl, dodecyl, tridecyl, tetradecyl, pentadecyl, hexadecyl, heptadecyl, octadecyl and positional isomers thereof.

$C_8$-$C_{14}$-Alkyl is a linear or branched alkyl radical having 8 to 14 carbon atoms. Examples thereof are octyl, 2-ethylhexyl, nonyl, decyl, 2-propylheptyl, undecyl, dodecyl, tridecyl, tetradecyl and positional isomers thereof.

$C_{10}$-$C_{18}$-Alkyl is a linear or branched alkyl radical having 10 to 18 carbon atoms. Examples thereof are decyl, 2-propylheptyl, undecyl, dodecyl, tridecyl, tetradecyl, pentadecyl, hexadecyl, heptadecyl, octadecyl and positional isomers thereof.

$C_{10}$-$C_{14}$-Alkyl is a linear or branched alkyl radical having 10 to 14 carbon atoms. Examples thereof are decyl, 2-propylheptyl, undecyl, dodecyl, tridecyl, tetradecyl and the positional isomers thereof.

$C_{12}$-$C_{18}$-Alkyl is a linear or branched alkyl radical having 12 to 18 carbon atoms. Examples thereof are dodecyl, tridecyl, tetradecyl, pentadecyl, hexadecyl, heptadecyl, octadecyl and positional isomers thereof.

$C_{12}$-Alkyl is dodecyl and the positional isomers thereof.

The remarks which follow regarding preferred embodiments, especially regarding preferred embodiments of the compounds I, the use thereof and the compositions comprising them, apply either taken alone or in any conceivable combination with one another. Unless anything is mentioned to the contrary, the remarks apply both to the inventive use and to the inventive washing and cleaning compositions.

The compounds I being used in accordance with the invention may be chemically pure substances or mixtures of different compounds I. In general, due to the production process therefor and the reactants used therein, which may be technical-grade products or product mixtures, mixtures of different compounds I will be involved, which differ, for example, in the definition of the variables R, R', n, x and/or y.

R and R' are preferably each independently $C_8$-$C_{16}$-alkyl, more preferably $C_8$-$C_{14}$-alkyl and in particular $C_{10}$-$C_{14}$-alkyl.

R and R' are preferably each a linear alkyl radical.

R and R' have preferably the same meaning.

In a specific embodiment, R and R' are each $C_{12}$-alkyl, especially n-dodecyl.

n is preferably from 15 to 100, more preferably from 20 to 80, even more preferably from 25 to 45 and especially from 30 to 40.

x and y are preferably each independently 0 or 1, more preferably 0.

The compounds I in which x and y are 0, can be prepared by condensation of polyethylene glycols (which must be terminated by OH groups) with alkylmercaptoethanol derivatives of the formula R—S—$CH_2CH_2$—OH or R'—S—$CH_2CH_2$—OH. Thioethers I in which x and/or y are different than 0 can be prepared by oxidation of the thioethers I in which x and y are each 0.

The present invention therefore further relates to a process for preparing compounds I, in which a polyethylene glycol of the formula

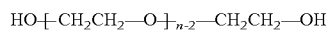

is reacted with an alkylmercaptoethanol derivative of the formula R—S—$CH_2CH_2$—OH or R'—S—$CH_2CH_2$—OH or a mixture thereof (when R and R' are different).

In the case that R and R' are different, the reaction of the polyethylene glycol with the different alkylmercaptoethanol derivatives of the formulae R—S—$CH_2CH_2$—OH and R'—S—$CH_2CH_2$—OH can be effected simultaneously or successively. In order to obtain defined products, the polyethylene glycol is first reacted with one mercaptoethanol, and only after the reaction with this first mercaptoethanol has ended is the product obtained reacted with the second mercaptoethanol.

This condensation with the mercaptoethanol is effected preferably under acidic catalysis. Suitable acids are, for example, p-toluenesulfonic acid, methanesulfonic acid, sulfuric acid, phosphoric acid and acidic ion exchangers. During the reaction, the water of reaction formed is preferably removed, for example by azeotropic distillation or stripping with an inert gas. If the water of reaction is to be removed by azeotropic distillation, the condensation is advantageously performed in a solvent which forms a minimum azeotrope with water, such as toluene or the xylenes. On completion of conversion, the product mixture obtained can be neutralized if desired.

The sulfur atom in the thioether obtained can be oxidized to the monosulfoxide (x=1, y=0 or vice versa) disulfoxide (x, y=1) or disulfone (x, y=2) by means of customary oxidizing agents, such as hydrogen peroxide, manganese dioxide, a permanganate, m-chloroperbenzoic acid or a perchlorate. Whether the oxidation proceeds up to the mono- or disulfoxide or up to the sulfone can be determined by factors including the selection of the oxidizing agent, the concentration thereof and the reaction temperature.

The polyethylene glycols used are commercially available. They can be obtained, for example, by polymerization of ethylene oxide or by addition of ethylene oxide onto ethylene glycol.

The alkylmercaptoethanol derivatives are likewise commercially available. They can be obtained, for example, by addition of thioethylene glycol onto an alkene.

The compounds I can be used in accordance with the invention in the form of the solution obtained in the preparation thereof. However, they are preferably isolated by means of customary processes and purified if desired.

The compounds of the formula I are usable in principle in all common washing and cleaning compositions.

In the context of the present invention, washing compositions are understood to mean those compositions which are used for cleaning of flexible materials with high absorptivity, for example of materials with textile character, whereas cleaning compositions in the context of the present invention are understood to mean those compositions which are used for cleaning of materials with a continuous surface, i.e. with a surface which has only few and small pores, if any, and as a result has only low absorptivity, if any.

Examples of flexible materials with high absorptivity are those which comprise or consist of natural, synthetic or semi-synthetic fiber materials, and which accordingly generally at least partially have textile character. The fibrous materials, or those consisting of fibers, may in principle be present in any form which occurs in use or in production and processing. For example, fibers may be present in unordered form in the form of staple or aggregate, in ordered to form in the form of fibers, yarns, threads, or in the form of fabrics such as nonwovens, lodens or felt, wovens, knits, in all conceivable binding types. The fibers may be raw fibers or fibers in any processing state. Examples are natural protein or cellulose fibers, such as wool, silk, cotton, sisal, hemp or coconut fibers, or synthetic fibers, for example polyester, polyamide or polyacrylonitrile fibers.

Examples of materials which have only few and small pores, if any, and have only low absorptivity, if any, are metal, glass, enamel or ceramic. Typical objects made of these materials are, for example, metal sinks, cutlery, glass and porcelain dishware, bathtubs, washbasins, tiles, flags, hardened synthetic resins, for example decorative melamine resin surfaces on kitchen furniture, or finished metal surfaces, for example refrigerators and automobile bodies, printed circuit boards, microchips, sealed or varnished wood, for example parquet or wall paneling, window frames, doors, plastic coverings such as floor coverings made of PVC or hard rubber, or hard or soft foams with substantially continuous surfaces.

Examples of cleaning compositions which comprise the compounds I comprise dishwashing compositions, such as manual dishwashing compositions or machine dishwashing compositions (=dishwashing compositions for the machine dishwasher), metal degreasers, glass cleaners, floor cleaners, all-purpose cleaners, high-pressure cleaners, neutral cleaners, alkaline cleaners, acidic cleaners, spray degreasers, dairy cleaners, industrial kitchen cleaners, equipment cleaners in industry, especially in the chemical industry, cleaners in car washes, and also domestic all-purpose cleaners.

The compounds I are preferably used in dishwashing compositions. They are more preferably used in machine dishwashing compositions. Among these, preference is given to dishwashing compositions, especially machine dishwashing compositions, with rinse aid function.

The washing and cleaning compositions which comprise the compounds I are preferably solid at room temperature (20° C.).

The solid washing and cleaning compositions may be pulverulent or tableted products ("tabs"). They are preferably tableted products ("tabs"). More preferably, they are tableted dishwashing compositions, especially tableted machine dishwashing compositions.

Tableted dishwashing compositions may be simple tabs or else what are called "2 in 1", "3 in 1", "5 in 1", "7 in 1" and the like products (multifunctional products; generally spoken "x in 1" products with x=an integer). Further details of these formulations can be found in Hermann G. Hauthal, G. Wagner (eds.), Reinigungs- and Pflegemittel im Haushalt [Domestic Cleaning and Care Compositions], Verlag für chemische Industrie, H. Ziolkowsky GmbH, Augsburg 2003, chapter 4.2, pages 161-184. "2 in 1" products comprise, as well as the customary constituents of machine dishwashing compositions, additionally a rinse aid. "3 in 1" products also comprise a water softener. "5 in 1" products generally also comprise a glass protector and a rinsing power enhancer. "7 in 1" products also comprise a precious metal brightener and an encrustation remover.

The compounds I are preferably used in tableted multifunctional machine dishwashing compositions, where they completely or partially replace the customary rinse aids.

The compounds I have an effect both as a surfactant and as a rinse aid. The invention therefore also relates to the use of the compounds I as a surfactant and/or as a rinse aid. More particularly, the invention relates to the use of the compounds I as a surfactant with rinse aid effect or as a rinse aid surfactant.

The compounds I used in accordance with the invention are notable especially for excellent deposition-inhibiting action in the case of use in the rinse cycle of the machine dishwasher. They have inhibiting action both with respect to inorganic deposits and with respect to organic deposits. The inorganic deposits are especially calcium and magnesium phosphate, calcium and magnesium carbonate, calcium and magnesium silicate and/or calcium and magnesium phosphonate, which form from the calcium and magnesium salts present in the water and the builders present in customary dishwashing compositions. The organic deposits are especially soil constituents from the rinse liquor, such as protein, starch and grease deposits. The compounds I used in accordance with the invention are also effective against what are called carry-over deposits, which originate from the residual amount of water in the bottom of the dishwasher and comprise, inter alia, dishwashing composition residues and possibly also soil residues from the previous wash cycle of the machine dishwasher.

The invention further provides washing or cleaning compositions which comprise at least one compound of the formula I. With regard to suitable washing or cleaning compositions, reference is made to the above remarks.

The washing and cleaning compositions are preferably dishwashing compositions, among which machine dishwashing compositions are preferred. These are especially dishwashing compositions, especially machine dishwashing compositions, with rinse aid function.

The inventive washing and cleaning composition is preferably solid at room temperature (20° C.). With regard to suitable and preferred solid washing and cleaning compositions, reference is made to the above remarks. More particularly, the inventive washing and cleaning compositions are tableted multifunctional machine dishwashing compositions.

The compounds I may be present therein in the rinse core; preferably, however, they are present as a solid in the tableted dishwashing composition.

The inventive dishwashing composition preferably comprises the following constituents:
a) at least one compound of the formula I;
b) at least one builder (also referred to as a sequestrant, framework substance, complexing agent, chelator, chelating agent or softener);
c) optionally at least one enzyme; and
d) optionally at least one bleach; and
e) optionally at least one further additive preferably selected from surfactants other than a), bases, corrosion inhibitors, defoamers, dyes, fragrances, fillers, tableting aids, disintegrants, thickeners, solubilizers, organic solvents and water.

These constituents are preferably present in the inventive dishwashing composition in the following ratios:
a) at least one compound of the formula I: from 0.1 to 20% by weight;
b) at least one builder: from 5 to 80% by weight;
c) at least one enzyme: from 0 to 8% by weight;
d) at least one bleach: from 0 to 30% by weight; and
e) at least one further additive: from 0 to 50% by weight.

The percentages by weight are based on the total weight of the dishwashing composition. The weights from a) to e) add up to 100% by weight.

The inventive dishwashing composition more preferably comprises at least one enzyme.

More preferably, the abovementioned constituents are present in the inventive dishwashing composition in the following ratios:
a) at least one compound of the formula I: from 0.1 to 10% by weight;
b) at least one builder: from 20 to 80% by weight;
c) at least one enzyme: from 0.1 to 6% by weight;
d) at least one bleach: from 0 to 30% by weight; and
e) at least one further additive: from 0 to 50% by weight.

Even more preferably, the inventive dishwashing composition also comprises at least one bleach.

Even more preferably, the abovementioned constituents are present in the inventive dishwashing composition in the following ratios:
a) at least one compound of the formula I: from 0.1 to 10% by weight;
b) at least one builder: from 20 to 80% by weight;
c) at least one enzyme: from 0.1 to 6% by weight;
d) at least one bleach: from 5 to 25% by weight; and
e) at least one further additive: from 0 to 50% by weight.

With regard to suitable and preferred compounds I, reference is made to the above remarks.

Builders, which are sometimes also referred to as sequestrants, structural substances, complexing agents, chelators, chelating agents or softeners, bind alkaline earth metals and other water-soluble metal salts without precipitating. They help to break up soil, disperse soil components, help to detach soil and in some cases themselves have a washing effect. In addition, when they are solid and are used in pulverulent formulations, they keep the powder free-flowing.

Suitable builders may be either organic or inorganic in nature. Examples are aluminosilicates, carbonates, phosphates and polyphosphates, polycarboxylic acids, polycarboxylates, hydroxycarboxylic acids, phosphonic acids, e.g. hydroxyalkylphosphonic acids, phosphonates, aminopolycarboxylic acids and salts thereof, and polymeric compounds containing carboxylic acid groups and salts thereof.

Suitable inorganic builders are, for example, crystalline or amorphous aluminosilicates with ion-exchanging properties, such as zeolites. Various types of zeolites are suitable, especially zeolites A, X, B, P, MAP and HS in the sodium form thereof, or in forms in which Na has been partially exchanged for other cations such as Li, K, Ca, Mg or ammonium. Suitable zeolites are described, for example, U.S. Pat. No. 4,604,224. Crystalline silicates suitable as builders are, for example, disilicates or sheet silicates, e.g. 5-$Na_2Si_2O_5$ or B—$Na_2Si_2O_5$ (SKS 6 or SKS 7). The silicates can be used in the form of their alkali metal, alkaline earth metal or ammonium salts, preferably as sodium, lithium and magnesium silicates. Amorphous silicates, for example sodium metasilicate which has a polymeric structure, or amorphous disilicate (Britesil® H 20, manufacturer: Akzo), are likewise usable. Among these, preference is given to sodium disilicate.

Suitable inorganic builder substances based on carbonate are carbonates and hydrogencarbonates. These can be used in the form of their alkali metal, alkaline earth metal or ammonium salts. Preference is given to using sodium, lithium and magnesium carbonates or sodium, lithium and magnesium hydrogencarbonates, especially sodium carbonate and/or sodium hydrogencarbonate.

Customary phosphates used as inorganic builders are alkali metal orthophosphates and/or polyphosphates, for example pentasodium triphosphate.

Suitable organic builders are, for example, $C_4$-$C_{30}$-di-, -tri- and -tetracarboxylic acids, for example succinic acid, propanetricarboxylic acid, butanetetracarboxylic acid, cyclopentanetetracarboxylic acid, and alkyl- and alkenylsuccinic acids with $C_2$-$C_{20}$-alkyl or -alkenyl radicals.

Suitable organic builders are also hydroxycarboxylic acids and polyhydroxycarboxylic acids (sugar acids). These include $C_4$-$C_{20}$-hydroxycarboxylic acids, for example malic acid, tartaric acid, glutonic acid, mucic acid, lactic acid, glutaric acid, citric acid, tartronic acid, glucoheptonic acid, lactobionic acid, and sucrosemono-, -di- and -tricarboxylic acid. Among these, preference is given to citric acid and salts thereof.

Suitable organic builders are also phosphonic acids, for example hydroxyalkylphosphonic acids, aminophosphonic acids and the salts thereof. These include, for example, phosphonobutanetricarboxylic acid, aminotris-methylenephosphonic acid, ethylenediaminetetraethylenephosphonic acid, hexamethylenediaminetetramethylenephosphonic acid, diethylenetriamine-pentamethylenephosphonic acid, morpholinomethanediphosphonic acid, 1-hydroxy-$C_1$- to $C_{10}$-alkyl-1,1-diphosphonic acids such as 1-hydroxyethane-1,1-diphosphonic acid. Among these, preference is given to 1-hydroxyethane-1,1-diphosphonic acid and salts thereof.

Suitable organic builders are additionally aminopolycarboxylic acids, such as nitrilotriacetic acid (NTA), nitrilomonoacetic dipropionic acid, nitrilotripropionic acid, β-alaninediacetic acid (β-ADA), ethylenediaminetetraacetic acid (EDTA), diethylenetriaminepentaacetic acid, 1,3-propylenediaminetetraacetic acid, 1,2-propylenediaminetetraacetic acid, N-(alkyl)ethylenediaminetriacetic acid, N-(hydroxyalkyl)ethylenediaminetriacetic acid, ethylenediaminetriacetic acid, cyclohexylene-1,2-diaminetetraacetic acid, iminodisuccinic acid, ethylenediaminedisuccinic acid, serinediacetic acid, isoserinediacetic acid, L-asparaginediacetic acid, L-glutaminediacetic acid, methylglycinediacetic acid (MGDA), and the salts of the aforementioned aminopolycarboxylic acids. Among these, preference is given to L-glutaminediacetic acid, methylglycinediacetic acids and salts thereof.

Suitable organic builders are additionally polymeric compounds containing carboxylic acid groups, such as acrylic acid homopolymers. These preferably have a number-average molecular weight in the range from 800 to 70 000 g/mol, more preferably from 900 to 50 000 g/mol, particularly from 1000 to 20 000 g/mol, especially 1000 to 10 000 g/mol. The term "acrylic acid homopolymer" also comprises polymers in which some or all of the carboxylic acid groups are present in neutralized form. These include acrylic acid homopolymers in which some or all of the carboxylic acid groups are present in the form of alkali metal salts or ammonium salts. Preference is given to acrylic acid homopolymers in which the carboxylic acid groups are protonated or in which some or all of the carboxylic acid groups are in the form of sodium salts.

Suitable polymeric compounds containing carboxylic acid groups are also oligomaleic acids, as described, for example, in EP-A 451 508 and EP-A 396 303. Suitable polymeric compounds containing carboxylic acid groups are also terpolymers of unsaturated $C_4$-$C_8$-dicarboxylic acids, where the polymerized comonomers may include monoethylenically unsaturated monomers from group (i) specified below in amounts of up to 95% by weight, from group (ii) in amounts of up to 60% by weight and from group (iii) in amounts of up to 20% by weight. Suitable unsaturated $C_4$-$C_8$-dicarboxylic acids in this context are, for example, maleic acid, fumaric acid, itaconic acid and citraconic acid. Preference is given to maleic acid. Group (i) comprises monoethylenically unsaturated $C_3$-$C_8$-monocarboxylic acids, for example acrylic acid, methacrylic acid, crotonic acid and vinylacetic acid. Group (i), preference is given to using acrylic acid and methacrylic acid. Group (ii) comprises monoethylenically unsaturated $C_2$-$C_{22}$-olefins, vinyl alkyl ethers with $C_1$-$C_8$-alkyl groups, styrene, vinyl esters of $C_1$-$C_8$-carboxylic acids, (meth)acrylamide and vinylpyrrolidone. From group (ii), preference is given to using $C_2$-$C_6$-olefins, vinyl alkyl ethers with $C_1$-$C_4$-alkyl groups, vinyl acetate and vinyl propionate. If the polymers of group (ii) comprise vinyl esters in polymerized form, they may also be present partly or fully hydrolyzed to vinyl alcohol structural units. Suitable co- and terpolymers are known, for example, from U.S. Pat. No. 3,887,806 and DE-A 4313909. Group (iii) comprises (meth)acrylic esters of $C_1$-$C_8$-alcohols, (meth)acrylonitrile, (meth)acrylamides of $C_1$-$C_8$-amines, N-vinylformamide and N-vinylimidazole.

Suitable polymeric compounds containing carboxylic acid groups are also homopolymers of the monoethylenically unsaturated $C_3$-$C_8$-monocarboxylic acids, for example acrylic acid, methacrylic acid, crotonic acid and vinylacetic acid, especially of acrylic acid and methacrylic acid, copolymers of dicarboxylic acids, for example copolymers of maleic acid and acrylic acid in a weight ratio of 10:90 to 95:5, more preferably those in a weight ratio of from 30:70 to 90:10 with molar masses of from 1000 to 150 000; terpolymers of maleic acid, acrylic acid and a vinyl ester of a $C_1$-$C_3$-carboxylic acid in a weight ratio of from 10 (maleic acid):90 (acrylic acid+vinyl ester) to 95 (maleic acid):10 (acrylic acid+vinyl ester), where the weight ratio of acrylic acid to the vinyl ester may vary within the range from 30:70 to 70:30; copolymers of maleic acid with $C_2$-$C_8$-olefins in a molar ratio of from 40:60 to 80:20, particular preference being given to copolymers of maleic acid with ethylene, propylene or isobutene in a molar ratio of 50:50.

Suitable polymeric compounds containing carboxylic acid groups are also copolymers of 50 to 98% by weight of ethylenically unsaturated weak carboxylic acids with 2 to 50% by weight of ethylenically unsaturated sulfonic acids, as described, for example, in EP-A-0877002. Suitable weak ethylenically unsaturated carboxylic acids are especially $C_3$-$C_6$-monocarboxylic acids, such as acrylic acid and methacrylic acid. Suitable ethylenically unsaturated sulfonic acids are 2-acetylamidomethyl-1-propanesulfonic acid, 2-methacrylamido-2-methyl-1-propanesulfonic acid, 2-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propene-1-sulfonic acid, styrenesulfonic acid, vinylsulfonic acid, 3-sulfopropyl acrylate, 3-sulfopropyl methacrylate, sulfomethylacrylamide, sulfomethylmethacrylamide and salts of these acids. The copolymers may also comprise, in copolymerized form, 0 to 30% by weight of ethylenically unsaturated $C_4$-$C_8$-dicarboxylic acids, such as maleic acid, and 0 to 30% by weight of at least one monomer which is copolymerizable with the aforementioned monomers. The latter are, for example, $C_1$-$C_4$-alkyl esters of (meth)acrylic acid, $C_1$-$C_4$-hydroxyalkyl esters of (meth)acrylic acid, acrylamide, alkyl-substituted acrylamide, N,N-dialkyl-substituted acrylamide, vinylphosphonic acid, vinyl acetate, allyl alcohols, sulfonated allyl alcohols, styrene and other vinylaromatics, acrylonitrile, N-vinylpyrrolidone, N-vinylformamide, N-vinylimidazole or N-vinylpyridine. The weight-average molecular weight of these copolymers is within the range from 3000 to 50 000. Particularly suitable copolymers are those with about 77% by weight of at least one ethylenically unsaturated $C_3$-$C_6$-monocarboxylic acid and about 23% by weight of at least one ethylenically unsaturated sulfonic acid.

Graft polymers of unsaturated carboxylic acids onto low molecular weight carbohydrates or hydrogenated carbohydrates, cf. U.S. Pat. No. 5,227,446, DE-A 4415623 and DE-A 4313909, are likewise suitable. Suitable unsaturated carboxylic acids in this context are, for example, maleic acid, fumaric acid, itaconic acid, citraconic acid, acrylic acid, methacrylic acid, crotonic acid and vinylacetic acid and also mixtures of acrylic acid and maleic acid, which are grafted on in amounts of 40 to 95% by weight, based on the component to be grafted. For modification, it is additionally possible for up to 30% by weight, based on the component to be grafted, of further monoethylenically unsaturated monomers to be present in polymerized form. Suitable modifying monomers are the abovementioned monomers of groups (ii) and (iii). Suitable graft bases are degraded polysaccharides, for example acidically or enzymatically degraded starches, inulins or cellulose, protein hydrolyzates and reduced (hydrogenated or hydrogenatingly aminated) degraded polysaccharides, for example mannitol, sorbitol, aminosorbitol and N-alkylglucamine, as are polyalkylene glycols with molar masses of up to $M_w$=5000, for example polyethylene glycols, ethylene oxide/propylene oxide or ethylene oxide/butylene oxide or ethylene oxide/propylene oxide/butylene oxide block copolymers and alkoxylated mono- or polyhydric $C_1$-$C_{22}$-alcohols (cf. U.S. Pat. No. 5,756,456).

Likewise suitable are polyglyoxylic acids, as described, for example, in EP-B-001004, U.S. Pat. No. 5,399,286, DE-A-4106355 and EP-A-656914. The end groups of the polyglyoxylic acids may have different structures.

Additionally suitable are polyamidocarboxylic acids and modified polyamidocarboxylic acids; these are, for example, known from EP-A-454126, EP-B-511037, WO-A-94/01486 and EP-A-581452.

Polyaspartic acids or cocondensates of aspartic acid with further amino acids, $C_4$-$C_{25}$-mono- or -dicarboxylic acids and/or $C_4$-$C_{25}$-mono- or -diamines can also be used as polymeric compounds containing carboxylic acid groups. Particular preference is given to using polyaspartic acids which have been prepared in phosphorus acids and have been modified with $C_6$-$C_{22}$-mono- or -dicarboxylic acids or with $C_6$-$C_{22}$-mono- or -diamines.

Among the polymeric compounds containing carboxylic acid groups, polyacrylic acids are preferred, including in partly or fully neutralized form.

Suitable organic builders are also iminodisuccinic acid, oxydisuccinic acid, aminopolycarboxylates, alkyl polyaminocarboxylates, aminopolyalkylenephosphonates, polyglutamates, hydrophobically modified citric acid for example agaric acid, poly-α-hydroxyacrylic acid, N-acylethylenediamine triacetates such as lauroylethylenediamine triacetate and alkylamides of ethylenediaminetetraacetic acid, such as EDTA tallow amide.

In addition, it is also possible to use oxidized starches as organic builders.

Preference is given to using, as component b), a mixture of different builders.

The mixture of different builders preferably comprises at least two of the following constituents: at least one carbonate (e.g. sodium carbonate), at least one silicate (e.g. sodium disilicate), at least one polymeric compound containing carboxylic acid groups or at least one polymeric compound which contains carboxylic acid groups of which all or some are present in neutralized form (e.g. polyacrylic acid), at least one (poly)hydroxycarboxylic acid or a salt thereof (e.g. citric acid or a citrate), at least one aminopolycarboxylic acid or a salt thereof (e.g. methylglycinediacetic acid or a salt thereof, e.g. a sodium salt thereof), at least one phosphonic acid (e.g. 1-hydroxyethane-1-(1,1-diphosphonic acid); HEDP), at least one phosphate. More preferably, the mixture comprises at least one carbonate, at least one silicate and at least one polymeric, optionally (partially) neutralized compound containing carboxylic acid groups, and optionally at least one of the following constituents: at least one (poly)hydroxycarboxylic acid or a salt thereof, at least one phosphonic acid, at least one phosphate. The mixture especially comprises at least one carbonate, at least one silicate, at least one polymeric, optionally (partially) neutralized compound containing carboxylic acid groups, at least one (poly)hydroxycarboxylic acid or a salt thereof, and at least one phosphonic acid, and optionally at least one phosphate.

In such a mixture, the constituents are present preferably in the following amounts:

b1) at least one carbonate: 10 to 50% by weight;
b2) at least one silicate, 1 to 10% by weight;
b3) at least one polymeric, optionally (partially) neutralized compound containing carboxylic acid groups: 5 to 20% by weight;
b4) at least one (poly)hydroxycarboxylic acid or a salt thereof: 0 to 50% by weight;
b5) at least one aminopolycarboxylic acid or a salt thereof: 0 to 60% by weight;
b6) at least one phosphonic acid: 0.2 to 1% by weight;
b7) at least one phosphate: 0 to 60% by weight.

The percentages by weight are based on the total weight of the builder. The weights from b1) to b7) add up to 100% by weight.

The enzymes are preferably selected from hydrolases, such as proteases, esterases, glucosidases, lipases, amylases, cellulases, mannanases, other glycosylhydrolases, and mixtures of the aforementioned enzymes. All these hydrolases contribute to dissolution and removal of soil from protein-, grease- or starch-containing stains. For bleaching, it is also possible to use oxidoreductases. Particularly suitable are active enzymatic ingredients obtained from bacterial strains or fungi, such as *Bacillus subtilis, Bacillus licheniformis, Streptomyces griseus* and *Humicola insolens*.

Suitable hydrolases are, for example, α-glucosidases (EC number 3.2.1.20), proteases (Ovozyme® (from Novozymes);

EC number 3.2.1.20), amylases [Purastar® (from Genencor), Termamyl® (from Novozymes), Stainzyme® (from Novozymes), Duramyl® (from Novozymes)], mannanases [Purabrite® (from Genencor), Mannastar® (from Genencor), Mannaway® (from Novozymes)] and cellulases [Carezyme® (from Novozymes), Celluzyme® (from Novozymes), Endolase®, Puradax® (from Genencor)]. The suitable amylases include especially α-amylases (EC number 3.2.1.1), iso-amylases, pullulanases and pectinases. The cellulases used are preferably cellobiohydrolases, endoglucanases and β-glucosidases, which are also referred to as cellobiases, or mixtures thereof. Since different cellulase types differ by their CMCase and Avicelase activities, it is possible to establish the desired activities by means of controlled mixtures of the cellulases.

Suitable lipases are esterases, such as Lipex and Lipolase. Examples of lipolytically active enzymes are the known cutinases.

Peroxidases or oxidases have also been found to be suitable in some cases.

The inventive dishwashing composition preferably comprises at least one protease and/or amylase.

The inventive dishwashing composition preferably comprises an enzyme mixture. Preference is given, for example, to enzyme mixtures which comprise or consist of the following enzymes:
protease and amylase,
protease and lipase (or lipolytically active enzymes),
protease and cellulase,
amylase, cellulase and lipase (or lipolytically active enzymes),
protease, amylase and lipase (or lipolytically active enzymes),
protease, lipase (or lipolytically active enzymes) and cellulase.

Particular preference is given to protease and/or amylase-containing mixtures.

Preferred proteases in the aforementioned mixtures are proteases of the subtilisin type (Savinase, etc.; EC number 3.4.21.62).

The enzymes may be adsorbed onto carriers in order to protect them from premature decomposition.

Optionally, the inventive washing and cleaning composition may also comprise enzyme stabilizers, for example calcium propionate, sodium formate or boric acids or salts thereof, and/or antioxidants.

The bleaches d) are preferably bleach systems which, in addition to bleaches, optionally also comprise bleach activators, bleach catalysts and/or bleach stabilizers.

Suitable bleaches are, for example, percarboxylic acids, for example diperoxododecanedicarboxylic acid, phthalimidopercaproic acid or monoperoxophthalic acid or -terephthalic acid, salts of percarboxylic acids, for example sodium percarbonate, adducts of hydrogen peroxide onto inorganic salts, for example sodium perborate monohydrate, sodium perborate tetrahydrate, sodium carbonate perhydrate or sodium phosphate perhydrate, adducts of hydrogen peroxide onto organic compounds, for example urea perhydrate, or of inorganic peroxo salts, for example alkali metal persulfates or peroxodisulfates.

Suitable bleach activators are, for example, polyacylated sugars, e.g. pentaacetylglucose; acyloxybenzenesulfonic acids and their alkali metal and alkaline earth metal salts, e.g. sodium p-nonanoyloxybenzenesulfonate or sodium p-benzoyloxybenzenesulfonate; N,N-diacylated and N,N,N',N'-tetraacylated amines, e.g. N,N,N',N'-tetraacetylmethylenediamine and -ethylenediamine (TAED), N,N-diacetylaniline, N,N-diacetyl-p-toluidine or 1,3-diacylated hydantoins such as 1,3-diacetyl-5,5-dimethylhydantoin; N-alkyl-N-sulfonylcarbonamides, e.g. N-methyl-N-mesylacetamide or N-methyl-N-mesylbenzamide; N-acylated cyclic hydrazides, acylated triazoles or urazoles, e.g. monoacetylmaleic hydrazide; O,N,N-trisubstituted hydroxylamines, e.g. O-benzoyl-N,N-succinylhydroxylamine, O-acetyl-N,N-succinylhydroxylamine or O,N,N-triacetylhydroxylamine; N,N'-diacylsulfurylamides, z.B. N,N'-dimethyl-N,N'-diacetylsulfurylamide or N,N'-diethyl-N,N'-dipropionylsulfurylamide; acylated lactams, for example acetylcaprolactam, octanoylcaprolactam, benzoylcaprolactam or carbonylbiscaprolactam; anthranil derivatives, for example 2-methylanthranil or 2-phenylanthranil; triacyl cyanurates, e.g. triacetyl cyanurate or tribenzoyl cyanurate; oxime esters and bisoxime esters, for example O-acetylacetone oxime or bisisopropyl iminocarbonate; carboxylic anhydrides, e.g. acetic anhydride, benzoic anhydride, m-chlorobenzoic anhydride or phthalic anhydride; enol esters, for example isopropenyl acetate; 1,3-diacyl-4,5-diacyloxyimidazolines, e.g. 1,3-diacetyl-4,5-diacetoxyimidazoline; tetraacetylglycoluril and tetrapropionylglycoluril; diacylated 2,5-diketopiperazines, e.g. 1,4-diacetyl-2,5-diketopiperazine; ammonium-substituted nitriles, for example N-methylmorpholinioacetonitrile methylsulfate; acylation products of propylenediurea and 2,2-dimethylpropylenediurea, e.g. tetraacetylpropylenediurea; α-acyloxypolyacylmalonamides, e.g. α-acetoxy-N,N'-diacetylmalonamide; diacyldioxohexahydro-1,3,5-triazines, e.g. 1,5-diacetyl-2,4-dioxohexahydro-1,3,5-triazine; benz-(4H)-1,3-oxazin-4-ones with alkyl radicals, e.g. methyl, or aromatic radicals, e.g. phenyl, in the 2 position.

A bleach system composed of bleaches and bleach activators may optionally also comprise bleach catalysts. Suitable bleach catalysts are, for example, quaternized imines and sulfonimines, which are described, for example, in U.S. Pat. No. 5,360,569 and EP-A 453 003. Particularly effective bleach catalysts are manganese complexes, which are described, for example, in WO-A 94/21777. In the case of use thereof in the washing and cleaning compositions, such compounds are incorporated at most in amounts up to 1.5% by weight, especially up to 0.5% by weight, and in the case of very active manganese complexes in amounts up to 0.1% by weight. In addition to the described bleach system composed of bleaches, bleach activators and optionally bleach catalysts, it is also possible to use systems with enzymatic peroxide release or photoactivated bleach systems for the inventive washing and cleaning compositions.

Surfactants from group e) other than component a) may be cationic, anionic, zwitterionic or nonionic.

Suitable nonionic surfactants are, for example, alkoxylated, advantageously ethoxylated, especially primary alcohols having preferably 8 to 18 carbon atoms and an average of 1 to 20, preferably 1 to 12, mol of ethylene oxide (EO) per mole of alcohol, in which the alcohol radical may be linear or preferably 2-methyl-branched, or may comprise linear and methyl-branched radicals in a mixture, as are typically present in oxo alcohol radicals. Especially preferred, however, are alcohol ethoxylates with linear radicals formed from alcohols of native origin having 12 to 18 carbon atoms, for example from coconut alcohol, palm alcohol, tallow fat alcohol or oleyl alcohol, and an average of 2 to 8 EO per mole of alcohol. The preferred ethoxylated alcohols include, for example, $C_{12}$-$C_{14}$-alcohols with 3 EO, 4 EO or 7 EO, $C_9$-$C_{11}$-alcohol with 7 EO, $C_{13}$-$C_{15}$-alcohols with 3 EO, 5 EO, 7 EO or 8 EO, $C_{12}$-$C_{18}$-alcohols with 3 EO, 5 EO or 7 EO and mixtures thererof, such as mixtures of $C_{12}$-$C_{14}$-alcohol with 3 EO and $C_{12}$-$C_{18}$-alcohol with 7 EO. The degrees of ethoxylation stated are statistical averages which, for a specific product, may be an integer or a fraction. Also suitable are alcohol ethoxylates which have a narrowed homolog distribution (narrow range ethoxylates, NRE). In addition to these nonionic surfactants, it is also possible to use fatty alcohols with more than 12 EQ. Examples thereof are tallow fat alcohol with 14 EO, 25 EO or 30 EO. It is also possible to use nonionic surfactants which comprise EO and PO groups together in the molecule. In this case, it is possible to use block copolymers with EO-PO block units or PO-EO block units, but also EO-PO-EO copolymers or P0-EO-PO copolymers. It will be appreciated that it is also possible to use mixed-alkoxylation nonionic surfactants in which EO and PO units are not in blockwise but in random distribution. Such products are obtainable by the simultaneous action of ethylene oxide and propylene oxide on fatty alcohols.

In addition, further nonionic surfactants used may also be alkyl glycosides of the general formula (1)

in which $R^a$ is a primary straight-chain or methyl-branched, especially 2-methyl-branched, aliphatic radical having 8 to 22, preferably 12 to 18, carbon atoms and G is a glycoside unit having 5 or 6 carbon atoms, preferably glucose. The degree of oligomerization y, which reports the distribution of monoglycosides and oligoglycosides, is any number between 1 and 10; y is preferably 1.2 to 1.4.

A further class of suitable nonionic surfactants, which can be used either as the sole nonionic surfactant or in combination with other nonionic surfactants, is that of alkoxylated, preferably ethoxylated or ethoxylated and propoxylated, fatty acid alkyl esters, preferably having 1 to 4 carbon atoms in the alkyl chain, especially fatty acid methyl esters as described, for example, in Japanese patent application JP 58/217598, or which are preferably prepared by the process described in international patent application WO-A-90/13533.

Nonionic surfactants of the amine oxide type, for example N-cocoalkyl-N,N-dimethylamine oxide and N-tallowalkyl-N,N-dihydroxyethylamine oxide, and of the fatty acid alkanolamide type, may also be suitable. The amount of these nonionic surfactants is preferably not more than that of the ethoxylated fatty alcohols, especially not more than half thereof.

Further suitable surfactants are polyhydroxy fatty acid amides of the formula (2)

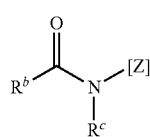

in which $R^b C(=O)$ is an aliphatic acyl radical having 6 to 22 carbon atoms, $R^c$ is hydrogen, an alkyl or hydroxyalkyl radical having 1 to 4 carbon atoms, and [Z] is a linear or branched polyhydroxyalkyl radical having 3 to 10 carbon atoms and 3 to 10 hydroxyl groups. The polyhydroxy fatty acid amides are known substances which can be obtained typically by reductive amination of a reducing sugar with ammonia, an alkylamine or an alkanolamine, and subsequent acylation with a fatty acid, a fatty acid alkyl ester or a fatty acid chloride.

The group of the polyhydroxy fatty acid amides also includes compounds of the formula (3)

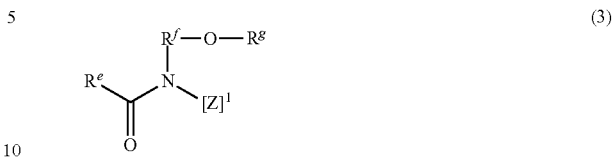

in which $R^e$ is a linear or branched alkyl or alkenyl radical having 7 to 12 carbon atoms, $R^f$ is a linear, branched or cyclic alkylene radical having 2 to 8 carbon atoms or an arylene radical having 6 to 8 carbon atoms, and $R^g$ is a linear, branched or cyclic alkyl radical or an aryl radical or an oxyalkyl radical having 1 to 8 carbon atoms, preference being given to $C_1$-$C_4$-alkyl or phenyl radicals, and $[Z]^1$ is a linear polyhydroxyalkyl radical, the alkyl chain of which has been substituted by at least two hydroxyl groups, or alkoxylated, preferably ethoxylated or propoxylated, derivatives of this radical. $[Z]^1$ is preferably obtained by reductive amination of a sugar, for example glucose, fructose, maltose, lactose, galactose, mannose or xylose. The N-alkoxy- or N-aryloxy-substituted compounds can then be converted, for example according to WO-A-95/07331, to the desired polyhydroxy fatty acid amides by reaction with fatty acid methyl esters in the presence of an alkoxide as a catalyst.

Suitable anionic surfactants are, for example, those of the sulfonate and sulfate type. Useful surfactants of the sulfonate type preferably include $C_9$-$C_{13}$-alkylbenzenesulfonates, olefinsulfonates, i.e. mixtures of alkene- and hydroxyalkanesulfonates and disulfonates, as obtained, for example, from $C_{12}$-$C_{18}$-monoolefins with terminal or internal double bonds by sulfonation with gaseous sulfur trioxide and subsequent alkaline or acidic hydrolysis of the sulfonation products. Also suitable are alkanesulfonates, which are obtained from $C_{12}$-$C_{18}$-alkanes, for example, by sulfochlorination or sulfoxidation with subsequent hydrolysis or neutralization. Equally suitable are also the esters of α-sulfo fatty acids (ester sulfonates), for example the α-sulfonated methyl esters of hydrogenated coconut fatty acids, palm kernel fatty acids or tallow fatty acids.

Further suitable anionic surfactants are sulfonated fatty acid glyceryl esters. Fatty acid glyceryl esters are understood to mean the mono-, di- and triesters and mixtures thereof, as obtained in the preparation by esterification of a monoglycerol with 1 to 3 mol of fatty acid, or in the transesterification of triglycerides with 0.3 to 2 mol of glycerol. Preferred sulfonated fatty acid glyceryl esters are the sulfonation products of saturated fatty acids having 6 to 22 carbon atoms, for example of caproic acid, caprylic acid, capric acid, myristic acid, lauric acid, palmitic acid, stearic acid or behenic acid.

Preferred alk(en)yl sulfates are the alkali metal salts and especially the sodium salts of the sulfuric monoesters of the $C_{12}$-$C_{18}$ fatty alcohols, for example of coconut fatty alcohol, tallow fatty alcohol, lauryl alcohol, myristyl alcohol, cetyl alcohol or stearyl alcohol, or of the $C_{10}$-$C_{20}$ oxo alcohols, and those monoesters of secondary alcohols of these chain lengths. Additionally preferred are alk(en)yl sulfates of the chain length mentioned, which comprise a synthetic straight-chain alkyl radical which has been produced on a petrochemical basis and which has analogous degradation behavior to the equivalent compounds based on fatty chemical raw materials. From the point of view of washing, the $C_{12}$-$C_{16}$-alkyl sulfates and $C_{12}$-$C_{15}$-alkyl sulfates, and also $C_{14}$-$C_{15}$-alkyl sulfates, are preferred. 2,3-Alkyl sulfates, which are prepared, for example, according to U.S. Pat. No. 3,234,258 or 5,075,041 and can be obtained as commercial products from Shell Oil Company under the DAN® name, are also suitable anionic surfactants.

The sulfuric monoesters of the straight-chain or branched $C_7$-$C_{21}$-alcohols which have been ethoxylated with 1 to 6 mol of ethylene oxide, such as 2-methyl-branched $C_9$-$C_{11}$-alcohols with an average of 3.5 mol of ethylene oxide (EO), or $C_{12}$-$C_{18}$ fatty alcohols with 1 to 4 EO, are also suitable. Owing to their high foaming level, they are used in cleaning compositions only in relatively small amounts, for example in amounts of 1 to 5% by weight.

Further suitable anionic surfactants are also the salts of alkylsulfosuccinic acid, which are also referred to as sulfosuccinates or as sulfosuccinic esters, and which are monoesters and/or diesters of sulfosuccinic acid with alcohols, preferably fatty alcohols and especially ethoxylated fatty alcohols. Preferred sulfosuccinates comprise $C_8$-$C_{18}$ fatty alcohol radicals or mixtures thereof. Especially preferred sulfosuccinates comprise a fatty alcohol radical which derives from ethoxylated fatty alcohols. Particular preference is given in turn to sulfosuccinates whose fatty alcohol radicals derive from ethoxylated fatty alcohols with a narrow homolog distribution. It is likewise also possible to use alk(en)ylsuccinic acid having preferably 8 to 18 carbon atoms in the alk(en)yl chain, or salts thereof.

Suitable anionic surfactants are also soaps. Saturated and unsaturated fatty acid soaps are suitable, such as the salts of lauric acid, myristic acid, palmitic acid, stearic acid, (hydrogenated) erucic acid and behenic acid, and especially soap mixtures derived from natural fatty acids, for example coconut fatty acids, palm kernel fatty acids, olive oil fatty acids or tallow fatty acids.

The anionic surfactants including the soaps may be present in the form of their sodium, potassium or ammonium salts, or as soluble salts of organic bases, such as mono-, di- or triethanolamine. The anionic surfactants are preferably in the form of their sodium or potassium salts, especially in the form of the sodium salts.

Cationic surfactants are, for example, ammonium salts such as $C_8$-$C_{16}$-dialkyldimethylammonium halides, dialkoxydimethylammonium halides or imidazolinium salts with a long-chain alkyl radical.

Amphoteric surfactants are, for example, derivatives of secondary or tertiary amines, for example $C_6$-$C_{18}$-alkyl betaines or $C_6$-$C_{15}$-alkyl sulfobetaines, or amine oxides such as alkyldimethylamine oxides.

Solvents present in component e) originate, for example, from the group of mono- or polyhydric alcohols, alkanolamines or glycol ethers. They are preferably selected from ethanol, n- or isopropanol, butanols, glycol, propane- or butanediol, glycerol, diglycol, propyl- or butyldiglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or monoethyl ether, diisopropylene glycol monomethyl or monoethyl ether, methoxy-, ethoxy- or butoxytriglycol, isobutoxyethoxy-2-propanol, 3-methyl-3-methoxybutanol, propylene glycol ter-tbutyl ether and mixtures of these solvents.

Useful foam inhibitors or defoamers of component e) may, for example, be soaps, paraffins or silicone oils, which may optionally be applied to carrier materials. Suitable bases of component e) are especially the carbonates mentioned above for the builders.

In an alternatively preferred embodiment of the invention, the inventive washing and cleaning compositions are in gel form. The washing and cleaning composition gels are preferably dishwashing composition gels, among which particular preference is given to machine dishwashing composition gels. More particularly, these are dishwashing composition gels, preferably machine dishwashing composition gels, with rinse aid function.

Washing and cleaning composition gels are understood to mean fluid compositions which, at room temperature (20° C.), have a viscosity higher than that of water, but are still sufficiently free-flowing that they can be dosed without any problem with conventional dosage aids. The inventive washing and cleaning composition gels preferably have a viscosity of 0.5 to 100, more preferably of 0.5 to 50 and especially of 1 to 30 Pa·s at 20° C.

The inventive dishwashing composition gel preferably comprises the following constituents:
a) at least one compound of the formula I;
b) at least one builder (also known as a sequestrant, structural substance, complexing agent, chelator, chelating agent or softener);
c) optionally at least one enzyme;
d) optionally at least one bleach;
e1) water;
e2) at least one thickener; and
e3) optionally at least one further additive preferably selected from surfactants other than a), bases, corrosion inhibitors, defoamers, dyes, fragrances, fillers, solubilizers and organic solvents.

These constituents are preferably present in the inventive dishwashing composition gel in the following ratios:
a) at least one compound of the formula I: from 0.1 to 20% by weight;
b) at least one builder: from 5 to 80% by weight;
c) at least one enzyme: from 0 to 8% by weight;
d) at least one bleach: from 0 to 30% by weight;
e1) water: from 10 to 90% by weight;
e2) at least one thickener: from 0.1 to 8% by weight; and
e3) at least one further additive: from 0 to 25% by weight.

The percentages by weight are based on the total weight of the dishwashing composition. The weights of a) to e3) add up to 100% by weight.

The inventive dishwashing composition more preferably comprises at least one enzyme.

The abovementioned constituents are more preferably present in the inventive dishwashing composition gel in the following ratios:
a) at least one compound of the formula I: from 0.1 to 10% by weight;
b) at least one builder: from 5 to 60% by weight;
c) at least one enzyme: from 0.1 to 6% by weight;
d) at least one bleach: from 0 to 30% by weight; and
e1) water: from 10 to 90% by weight;
e2) at least one thickener: from 0.1 to 6% by weight; and
e3) at least one further additive: from 0 to 25% by weight.

The percentages by weight are based on the total weight of the dishwashing composition. The weights of a) to e3) add up to 100% by weight.

The abovementioned constituents are even more preferably present in the inventive dishwashing composition gel in the following ratios:
a) at least one compound of the formula I: from 0.1 to 10% by weight;
b) at least one builder: from 5 to 40% by weight;
c) at least one enzyme: from 0.1 to 6% by weight;
d) at least one bleach: from 0 to 25% by weight; and e1) water: from 20 to 80% by weight;
e2) at least one thickener: from 0.3 to 5% by weight; and
e3) at least one further additive: from 0 to 25% by weight.

The percentages by weight are based on the total weight of the dishwashing composition. The weights of a) to e3) add up to 100% by weight.

The thickeners serve to impart the desired viscosity to the inventive dishwashing composition.

Any known thickener (rheology modifier) is suitable in principle, provided that it does not exert any adverse effect on the efficacy of the dishwashing composition. Suitable thickeners may either be of natural origin or of synthetic nature.

Examples of thickeners of natural origin are xanthan, carob flour, guar flour, carrageenan, agar, tragacanth, gum arabic, alginates, modified starches such as hydroxyethyl starch, starch phosphate esters or starch acetates, dextrins, pectins and cellulose derivatives, such as carboxymethylcellulose, hydroxyethylcellulose, hydroxypropylcellulose, hydroxypropylmethylcellulose, methylcellulose and the like.

Thickeners of natural origin are also inorganic thickeners, such as polysilicic acids and clay minerals, for example sheet silicates, and also the silicates mentioned for the builders.

Examples of synthetic thickeners are polyacrylic and polymethacrylic compounds, such as (partly) crosslinked homopolymers of acrylic acid, for example homopolymers of acrylic acid which have been crosslinked with an allyl ether of sucrose or pentaerythritol, or with propylene (carbomers), for example the Carbopol® brands from BF Goodrich (e.g. Carbopol® 676, 940, 941, 934 and the like) or the Polygel® brands from 3V Sigma (e.g. Polygel® DA), copolymers of ethylenically unsaturated mono- or dicarboxylic acids, for example terpolymers of acrylic acid, methacrylic acid or maleic acid with methyl acrylate or ethyl acrylate and a (meth)acrylate which derives from long-chain ethoxylated alcohols, for example the Acusol® brands from Rohm & Haas (e.g. Acusol® 820 or 1206A), copolymers of two or more monomers which are selected from acrylic acid, methacrylic acid and the $C_1$-$C_4$-alkyl esters thereof, for example copolymers of methacrylic acid, butyl acrylate and methyl methacrylate or of butyl acrylate and methyl methacrylate, for example the Aculyn® and Acusol® brands from Rohm & Haas (e.g. Aculyn® 22, 28 or 33 and Acusol® 810, 823 and 830), or crosslinked high molecular weight acrylic acid copolymers, for example copolymers of $C_{10}$-$C_{30}$-alkyl acrylates with one or more comonomers selected from acrylic acid, methacrylic acid and the $C_1$-$C_4$-alkyl esters thereof, said copolymers having been crosslinked with an allyl ether of sucrose or pentaerythritol (e.g. Carbopol® ETD 2623, Carbopol® 1382 or Carbopol® AQUA 30 from Rohm & Haas).

Examples of synthetic thickeners are also reaction products of maleic acid polymers with ethoxylated long-chain alcohols, for example the Surfonic L series from Texaco Chemical Co. or Gantrez AN-119 from ISP; polyethylene glycols, polyamides, polyimines and polycarboxylic acids.

Also suitable are mixtures of the abovementioned thickeners.

Preferred thickeners are xanthans and the abovementioned polyacrylic and polymethacrylic compounds.

With regard to suitable and preferred components a) to d) and e3), reference is made to the above remarks, The compounds I used in accordance with the invention have no strong tendency, if any, to form foam, they have a good deposit-inhibiting action on dishware washed therewith and they are not hydrolysis-labile. They can also be formulated efficiently into solid washing and cleaning compositions.

The invention also relates to compounds of the formula I.1

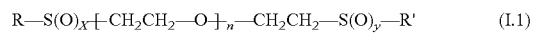

$$R-S(O)_x-[-CH_2CH_2-O-]_n-CH_2CH_2-S(O)_y-R' \quad (I.1)$$

in which
R and R' are each independently $C_6$-$C_{18}$-alkyl;
n is from 11 to 150; and
x and y are each 0, 1 or 2;
where x and y are not both 0.

In the inventive compounds I.1, R and R' are preferably each independently $C_8$-$C_{16}$-alkyl, more preferably $C_8$-$C_{14}$-alkyl and especially $C_{10}$-$C_{14}$-alkyl.

R and R' are preferably each a linear alkyl radical.

R and R' have preferably the same meaning.

R and R' are especially each $C_{12}$-alkyl, especially n-dodecyl.

n is preferably from 15 to 100, more preferably from 20 to 80, even more preferably from 25 to 45 and especially from 30 to 40.

x and y in compounds I.1 are preferably each independently 1 or 2. More preferably, both are 1 or both are 2.

The invention also relates to compounds of the formula I.2

$$R-S(O)_x-[-CH_2CH_2-O-]_n-CH_2CH_2-S(O)_y-R' \quad (I.2)$$

in which
R and R' are each independently $C_8$-$C_{18}$-alkyl, preferably $C_{10}$-$C_{18}$-alkyl and especially $C_{12}$-$C_{18}$-alkyl;
n is from 11 to 150; and
x and y are each 0, 1 or 2.

Preferably, R and R' in compounds I.2 are each a linear alkyl radical.

R and R' are preferably the same.

n is preferably from 15 to 100, more preferably from 20 to 80, even more preferably from 25 to 45 and especially from 30 to 40.

x and y in compounds I.2 are preferably each independently 0 or 1. More preferably, both are 0 or both are 1.

With regard to suitable processes for preparing compounds I.1 and I.2, reference is made to the above remarks.

The application is now illustrated further by the nonlimiting examples which follow.

EXAMPLES

1. Synthesis Examples 1.1 Preparation of 2-hydroxydodecyl ether-PEG 1000-2-hydroxydodecyl ether (comparative compound A)

In a 2 l autoclave from Mettler, the polyethylene glycol PEG 1000 to be alkoxylated (250 g, 1.0 mol eq) was admixed with an aqueous KOH solution which comprised 50% by weight of KOH (0.2% by weight of KOH based on the overall mixture, 1.4 g of 50% KOH). The amount of KOH was 0.2% by weight of the product to be prepared. While stirring, the mixture was dewatered at 100° C. and 20 mbar for 2 h. This was followed by purging three times with $N_2$, establishing an initial pressure of approx. 1.5 bar of $N_2$ and increasing the temperature to 140° C. Dodecene oxide (92.15 g, 2.0 mol eq.) was metered in such that the temperature remained between 135 and 145° C. This was followed by stirring at 140° C. for a further 24 h, purging with $N_2$, cooling to 80° C. and emptying the reactor. The crude product was degassed on the rotary evaporator at 100° C. (<20 mbar) for 2 h. This basic crude product was deionized with commercial magnesium silicates, which are subsequently filtered off (yield: 99%).

The light-colored product was identified with the aid of $^1$H NMR spectrum in CDCl$_3$ and gel permeation chromatography.

1.2 Preparation of 2,2'-di-(n-dodecylthio)-PEG 1500 (inventive compound B)

A 500 ml apparatus with a water trap was initially charged with a polyethylene glycol having a molecular weight of 1500 (150 g, 0.1 mol), para-toluenesulfonic acid (0.005 mol, 0.95 g) and toluene (approx. 150 ml). The reaction mixture was heated to reflux. Dodecylmercaptoethanol (0.25 mol, 61.6 g) was added dropwise. The water which formed (dist.: 3.8 ml/theoretical dist.: 4.5 ml) was removed by means of a water trap overnight. The reaction mixture was cooled, neutralized with sodium carbonate (0.005 mol, 0.53 g) and filtered, and the solvent was removed completely at 100° C. and 6 mbar. 165.4 g of a white solid product were obtained. The structure was determined by TAI NMR (93% OH groups converted). The residual amounts of toluene (<0.5%) and dodecylmercaptoethanol (0.3%) were determined by means of GC and the PEG content (2.5%) was measured by HPTLC.

1.3. Preparation of 2,2'-di-(n-dodecylsulfoxy)-PEG 1500 (inventive product C)

A 250 ml flask was initially charged with the product from example 1.2 (0.03 mol, 58.7 g) in water, which were heated to 70° C. Hydrogen peroxide (50%) (0.06 mol, 4.1 g) was added dropwise. The reaction mixture was stirred at 70° C. for 2 hours, then cooled and concentrated at 100° C. and 6 mbar. This gave 54 g of the title compound. The absence of hydrogen peroxide was checked by IR, and the conversion was determined by means of $^1$H NMR (86%).

1.4 Preparation of 2,2'-di-(n-octylthio)-PEG 1500 (inventive product D)

A 500 ml apparatus with a water trap was initially charged with polyethylene glycol of molecular weight 1500 (150 g, 0.1 mol), para-toluenesulfonic acid (0.005 mol, 0.95 g) and toluene (approx. 150 ml). The reaction mixture was heated to reflux. Octylmercaptoethanol (0.2 mol, 38.7 g) was added dropwise. The water which formed (dist.: 3.6 ml/theoretical dist.: 3.6 ml) was separated out by means of a water trap overnight. The reaction mixture was cooled, neutralized with sodium carbonate (0.005 mol, 0.53 g) and filtered, and the solvent was removed completely at 100° C. and 6 mbar. 172 g of a white solid product were obtained. The structure was determined by TAI-NMR (83% groups converted OH). Residual amounts of toluene (<0.5%) and octylmercaptoethanol (0.7%) were determined by means of GC and the PEG content (7%) was measured by HPTLC.

Method Description for TAI NMR:

In order to be able to (quantitatively) determine signals of primary and/or secondary alcohols superimposed in the $^1$H NMR spectrum, a sample in CDCl$_3$ is admixed with an excess of TAI (trichloroacetyl isocyanate). The isocyanate reacts immediately with the alcohol groups to give the carbamate. The compounds Cl$_3$CC(O)NHC(O)—OCH$_2$R or Cl$_3$CC(O)NHC(O)—OCH—RR' present therein have different, typical shifts for OCH$_2$ and OCHRR' in the $^1$H NMR spectrum.

The typical shift range for "primary carbamates" is 4.0 to 4.5 ppm, while that for "secondary carbamates" is 5.0 to 5.3 ppm.

2. Use Examples

2.1 Foam Volume in a Machine Dishwasher

The foam volume was determined indirectly by the measurement of foam formation via the speed of the spray arm of the machine dishwasher. For this purpose, 10 ml of beaten chicken egg, 19 g of a base dishwashing composition (48 parts sodium metasilicate×5H$_2$O, 45 parts sodium triphosphate, 5 parts sodium carbonate) and 1 g of the surfactant (A-D) were introduced into the dishwasher (Miele Desinfektor G 7735 CD MCU; programmable control unit MCU version S04.01). At different temperatures, the number of rotations of the spray arm was then measured. The spray arm is slowed down at a high foam level; it can work with the highest possible speed (approx. (125 rpm) at a low foam level. The peak speed of the dishwasher is usually approx. 125 rpm when no foam is present. The maximum speed in the machine dishwasher was set artificially in the present test (by means of bores on the spray arm, position of the nozzles), in order to obtain a broader range which allows better distinction of the products.

The rotation rate was measured at 40, 50 and 60° C. The table which follows lists the rotor speeds in rpm at different temperatures.

| Temperature | A | B | C | D |
|---|---|---|---|---|
| 40 [° C.] | 80 | 43 | 101 | 86 |
| 50 [° C.] | 88 | 50 | 102 | 97 |
| 60 [° C.] | 96 | 62 | 109 | 105 |

2.2 Rinse Aid Test

All examples were carried out with a base formulation of the following composition:
1 part by weight of protease (Ovozyme® 64 T)
0.2 part by weight of amylase (Stainzymee 12 T)
3 parts by weight of surfactant
10 parts by weight of polyacrylic acid with molar mass 4000 g/mol (Sokalan® PA 25 Cl)
10.5 parts by weight of sodium percarbonate
4 parts by weight of tetraacetylethylenediamine
2 parts by weight of sodium disilicate (Britesil® H 265 LC)
18.8 parts by weight of sodium carbonate
33 parts by weight of sodium citrate dihydrate
15 parts by weight of methylglycinediacetic acid trisodium salt (Trilon® M)
0.5 part by weight of 1-hydroxyethane-(1,1-diphosphonic acid) (HEDP; Cublen® K 8514 GR)

Ovozyme® and Stainzyme® are brand names of Novozymes, Sokalan® and Trilon0 are brand names of BASF SE, Britesil® is a brand name of PQ Corp., Cublen® is a brand name of Zschimmer&Schwarz Mohsdorf GmbH & Co KG.

All rinse aid tests were carried out in a Miele machine dishwasher (G1222 SCL). The program at 50° C. (R time 2) was selected for the wash cycle, and 65° C. for the rinse cycle. The tests were conducted with hardened water with water hardness 21° dH (Ca/Mg):HCO$_3$ (3:1):1.35. No separate rinse aid was added, and the incorporated water softener (ion exchanger) was not regenerated with regenerating salt. The abovementioned formulation was used in a dosage of 21 g in each case. For each rinse cycle, 100 g of ballast soil consisting of grease, protein and starch was added. The test dishware in each cleaning cycle was Cromargan knives, blue melamine plates and glasses. Between the rinse cycles, there was a wait period of one hour in each case, 10 min with the door closed, 50 min with the door open.

After the sixth rinse cycle had ended, the dishware was inspected visually in a darkened chamber under light behind an aperture plate, and assessed according to a scale of marks from 1 (=severe residues) to 10 (=no residues) with regard to deposits in the form of spots, streaks and films.

| Spotting marks | A | B | C | D |
|---|---|---|---|---|
| Knives | 2 | 3 | 1 | 3 |
| Glasses | 1 | 1 | 2 | 1 |
| Melamine plates | 3 | 3 | 4 | 3 |
| Total | 6 | 7 | 7 | 7 |

| Filming marks | A | B | C | D |
|---|---|---|---|---|
| Knives | 6 | 6 | 5 | 8 |
| Glasses | 5 | 5 | 5 | 8 |
| Melamine plates | 6 | 9 | 9 | 10 |
| Total | 17 | 20 | 19 | 26 |

The invention claimed is:

1. A washing or cleaning composition comprising
a) at least one compound of the formula I: from 0.1 to 10% by weight $$R-S(O)_x[CH_2CH_2-O]_n-CH_2CH_2-S(O)_y-R' \quad (I)$$

in which
R and R' are each independently $C_6$-$C_{18}$-alkyl;
n is from 11 to 150; and
x and y are each independently 0, 1 or 2;
b) at least one builder: from 20 to 80% by weight;
c) at least one enzyme: from 0.1 to 6% by weight;
d) at least one bleach: from 0 to 30% by weight; and
e) at least one further additive: from 0 to 50% by weight, wherein the further additive is selected from surfactants other than a), bases, corrosion inhibitors, defoamers, dyes, fragrances, fillers, tableting aids, disintegrants, thickeners, solubilizers, organic solvents and water;
based on the total weight of the washing or cleaning composition, and
wherein the washing or cleaning composition is a machine dishwashing composition.

2. The washing or cleaning composition according to claim 1, comprising the following constituents:
a) at least one compound of the formula I: from 0.1 to 10% by weight
b) at least one builder: from 20 to 80% by weight;
c) at least one enzyme: from 0.1 to 6% by weight;
d) at least one bleach: from 5 to 25% by weight; and
e) at least one further additive: from 0 to 50% by weight;
based on the total weight of the washing or cleaning composition.

3. A washing or cleaning composition comprising
a) at least one compound of the formula I $$R-S(O)_x[CH_2CH_2-O]_n-CH_2CH_2-S(O)_y-R' \quad (I)$$

in which
R and R' are each independently $C_6$-$C_{18}$-alkyl;
n is from 11 to 150; and
x and y are each independently 0, 1 or 2;

b) at least one builder;
c) optionally at least one enzyme;
d) optionally at least one bleach; and
e) optionally at least one further additive selected from surfactants other than a), bases, corrosion inhibitors, defoamers, dyes, fragrances, fillers, tableting aids, disintegrants, thickeners, solubilizers, organic solvents and water,
wherein component b) used is a mixture of different builders which comprises at least 2 of the following constituents: at least one carbonate, at least one silicate, at least one polymeric compound containing carboxylic acid groups or at least one polymeric compound which contains carboxylic acid groups of which all or some are present in neutralized form, at least one (poly)hydroxycarboxylic acid or a salt thereof, at least one aminopolycarboxylic acid or a salt thereof, at least one phosphonic acid, at least one phosphate, and
wherein the washing or cleaning composition is a machine dishwashing composition.

4. A washing or cleaning composition comprising
a) at least one compound of the formula I $$R-S(O)_x[CH_2CH_2-O]_n-CH_2CH_2-S(O)_y-R' \quad (I)$$

in which
R and R' are each independently $C_6$-$C_{18}$-alkyl;
n is from 11 to 150; and
x and y are each independently 0, 1 or 2;
and the following constituents:
b) at least one builder;
c) optionally at least one enzyme;
d) optionally at least one bleach;
e1) water;
e2) at least one thickener; and
e3) optionally at least one further additive selected from surfactants other than a), bases, corrosion inhibitors, defoamers, dyes, fragrances, fillers, solubilizers and organic solvents,
wherein the washing or cleaning composition is in gel form at room temperature.

5. The washing or cleaning composition according to claim 4, comprising the following constituents:
a) at least one compound of the formula I: from 0.1 to 20% by weight;
b) at least one builder: from 5 to 80% by weight;
c) at least one enzyme: from 0 to 8% by weight;
d) at least one bleach: from 0 to 30% by weight;
e1) water: from 10 to 90% by weight;
e2) at least one thickener: from 0.1 to 8% by weight; and
e3) at least one further additive: from 0 to 25% by weight; based on the total weight of the washing or cleaning composition.

6. The washing or cleaning composition according to claim 4, comprising the following constituents:
a) at least one compound of the formula I: from 0.1 to 10% by weight;
b) at least one builder: from 5 to 60% by weight;
c) at least one enzyme: from 0.1 to 6% by weight;
d) at least one bleach: from 0 to 30% by weight; and
e1) water: from 10 to 90% by weight;
e2) at least one thickener: from 0.1 to 6% by weight; and
e3) at least one further additive: from 0 to 25% by weight; based on the total weight of the washing or cleaning composition.

7. The washing or cleaning composition according to claim 4, comprising the following constituents:
- a) at least one compound of the formula I: from 0.1 to 10% by weight;
- b) at least one builder: from 5 to 40% by weight;
- c) at least one enzyme: from 0.1 to 6% by weight;
- d) at least one bleach: from 0 to 25% by weight; and
- e1) water: from 20 to 80% by weight;
- e2) at least one thickener: from 0.3 to 50% by weight; and
- e3) at least one further additive: from 0 to 25% by weight;

based on the total weight of the washing or cleaning composition.

8. A process for washing or cleaning which comprises contacting an object which with the washing or cleaning composition as claimed in claim 1.

9. The process according to claim 8, wherein the washing and cleaning composition is a dishwashing composition with rinse aid function.

10. The process according to claim 8, wherein the washing and cleaning composition is solid.

11. The process according to claim 8, wherein the washing and cleaning composition is in gel form.

12. The process according to claim 8, wherein the compound of the formula I is used as a surfactant.

13. The process according to claim 8, wherein the compound of the formula I is used as a rinse aid surfactant.

14. The process according to claim 8, wherein R and R' are each independently $C_8$-$C_{16}$-alkyl.

15. The process according to claim 14, wherein R and R' are each independently $C_{10}$-$C_{14}$-alkyl.

16. The process according to claim 8, wherein R and R' are each independently a linear alkyl radical.

17. The process according to claim 8, wherein R and R' have the same meaning.

18. The process according to claim 8, wherein n is from 25 to 45.

19. The process according to claim 8, wherein x and y are each 0 or 1.

20. The process according to claim 8, wherein x and y are each 0.

21. A process for preparing the washing or cleaning composition according to claim 1, comprising reacting a polyethylene glycol of the formula $$HO\text{−}[CH_2CH_2\text{−}O]_{n-2}\text{−}CH_2CH_2\text{−}OH$$

with an alkylmercaptoethanol derivative of the formula R—S—$CH_2CH_2$—OH or R'—S—$CH_2CH_2$—OH or a mixture thereof (when R and R' are different), where, in the case that R and R' are different, the polyethylene glycol can be reacted simultaneously or successively with the different alkylmercaptoethanol derivatives of the formulae R—S—$CH_2CH_2$—OH and R'—S—$CH_2CH_2$—OH.

22. The process according to claim 21, wherein the reaction is performed in the presence of an acidic catalyst.

* * * * *